United States Patent [19]

Gomez et al.

[11] 4,353,982

[45] Oct. 12, 1982

[54] IMMUNOCHEMICAL ASSAY FOR CREATINE KINASE-MB ISOENZYME

[75] Inventors: Magdalena U. Gomez, Wayne; Richard W. Wicks, Belleville, both of N.J.

[73] Assignee: Hoffmann-La Roche Inc., Nutley, N.J.

[21] Appl. No.: 139,042

[22] Filed: Apr. 10, 1980

[51] Int. Cl.³ .................... G01N 33/54; C12Q 1/50; G01T 1/00
[52] U.S. Cl. .................................. 435/7; 435/17; 435/810; 23/230 B; 424/1; 424/12
[58] Field of Search ............. 435/7, 17, 810, 815, 435/194; 424/1, 1.5, 8, 12; 23/230 B, 230.3

[56] References Cited

U.S. PATENT DOCUMENTS

| | | | |
|---|---|---|---|
| 3,932,221 | 1/1976 | Pfleiderer | 435/7 |
| 4,012,285 | 3/1977 | Pfleiderer | 435/4 |
| 4,049,496 | 9/1977 | Henry | 435/17 |
| 4,067,775 | 1/1978 | Wurzburg et al. | 435/17 |
| 4,237,219 | 12/1980 | Roberts | 435/7 |
| 4,260,678 | 4/1981 | Lepp et al. | 435/7 |

OTHER PUBLICATIONS

Schuurs et al., "Enzyme-Immunoassay", Clin. Chim. Acta., vol. 81, No. 1, (1977), pp. 1-40.
Roberts et al., "Radioimmunoassay for Canine Creatine Kinase Isoenzymes", Biochim. Biophys. Acta., vol. 480, (1977), pp. 521-526.
Roberts et al., "Immunologic Detection of Myocardial Infarction with a Radioimmunoassay for MB Creatine Kinase", Clin. Chim. Acta., vol. 83, (1978), pp. 141-149.
Neumeier et al., "Radioimmunoassay for Subunit Bin Isoenzymes CK-MB and CK-BB of Creatine Phosphokinnase", Clin. Chim. Acta., vol. 79, (1977), pp. 107-113.
Neumeier, D. et al., Clin. Chim. Acta, 73, 445, (1976).
Gerhardt, W. et al., Clin. Chim. Acta. 78, 29, (1977).
Zweig, M. H. et al., Clin. Chem. 24, 422, (1978).
Morin, L. G., Clin. Chem. 23, 205, (1977).

Primary Examiner—Thomas G. Wiseman
Attorney, Agent, or Firm—Jon S. Saxe; George M. Gould; John B. Wilson

[57] ABSTRACT

An immunochemical process and compositions for determining rapidly and accurately the amount of creatine kinase-MB isoenzyme (CK-MB) in biological fluids. The process employs a triple antibody technique which leads to the formation of an immuno-complex having a measurable label. This process and the resulting complex are useful in determining whether a patient has suffered a myocardial infarct.

43 Claims, No Drawings

IMMUNOCHEMICAL ASSAY FOR CREATINE KINASE-MB ISOENZYME

BACKGROUND OF THE INVENTION

Creatine kinase (CK) occurs in animal body fluids and tissue in the form of three known isoenzymes, designated CK-BB, CK-MM and CK-MB. Each of these three isoenzymes, namely CK-BB, CK-MM, and CK-MB, differs one from the other by virtue of containing a different combination of subunits designated M or B. CK-BB has two B subunits, CK-MM has 2 M subunits, and CK-MB has one M and one B subunit. Determining the mere presence of creatine kinase MB isoenzyme (CK-MB) in biological fluids, especially in a patient's serum, has become very useful in the diagnosis of myocardial infarction. (Galen, RS., Human Path 6: No. 2, 145–147, Apr. 1975).

A difficulty encountered in immunological methods for determining CK-MB in biological fluids is interference from CK-MM and CK-BB. Antibodies raised against CK-MM, CK-BB, or CK-MB by virtue of an identical subunit will react immunologically with CK-MB and CK-MM, with CK-MB and CK-BB, or with all three isoenzymes, respectively. Most biological fluids suspected of containing CK-MB will often contain CK-MM in an appreciable amount and CK-BB and CK-MB in a much lesser amount. As a result a problem encountered in the prior art in measuring CK-MB has been interferences from CK-BB and CK-MM.

Current methods including immunological ones for determining the presence of CK-MB and the disadvantages of such methods have recently been reported and reviewed (Current Problems in Cardiology, Vol. III, No. 12, March, 1979 p. 7–28). These methods have not been very satisfactory in resolving the difficulty of interference of CK-MM and CK-BB in the determination of CK-MB. Among these reported methods are immunological ones such as the enzyme immunoassay procedure of U.S. Pat. No. 4,067,775 wherein antibodies are used to inhibit the enzymatic activity of interfering substances and enzyme immunoprecipitin methods such as the ones described in U.S. Pat. Nos. 4,012,285 and 3,932,221 wherein CK isoenzymes are precipitated by antibodies.

The methods described in U.S. Pat. Nos. 4,012,285 and 3,932,221 employ single antibody complexes to precipitate differentially the various isoenzymes in an attempt to determine CK-MB indirectly. These methods require a determination of total CK activity before precipitation and the determination of residual CK activity after precipitation, with the difference in activities being a measure of CK-MB. The activities are determined by enzymatic assays. These methods are laborious and highly subjected to error by virtue of having to measure a difference between two quantities.

SUMMARY OF THE INVENTION

The present invention relates to a process and compositions for selectively determining directly the amount of CK-MB in a biological fluid sample containing CK-MB in combination with CK-MM and CK-BB.

The process comprises (a) incubating the sample with a first antibody raised in a first animal species, the first antibody capable of immunoreactively binding selectively one of the B or M subunits of the creatine kinase in the sample; with a second antibody raised in a second animal species, the second antibody capable of immunoreactively binding selectively as an immunoprecipitin the first antibody; and with a third antibody raised in an animal species other than the first animal species and labeled with a measurable label, the third antibody capable of immunoreactively binding selectively the other of said B or M subunits which the first antibody is capable of binding to provide as a precipitate a mixture of immunocomplexes containing labeled third antibody-creatine kinase-MB isoenzyme-first antibody-second antibody and creatine kinase isoenzyme-first antibody-second antibody; (b) isolating the precipitate; and (c) measuring the amount of label in the precipitate containing the immunocomplexes. By comparing the amount of measured label to a standard curve, one is able to determine the amount of CK-MB present in the biological fluid sample.

The invention processes employ a triple antibody technique wherein antibodies against CK-MM or CK-BB are effectively used to produce precipitable immunocomplexes which can be used to directly measure CK-MB. The invention processes provide for the use of a radioactive label for a radiometric assay, a more sensitive and efficient measure of CK-MB than other commonly employed detecting assay methods. The radiometric assay of the invention allows the possibility of detecting heretofore undetectable amounts of CK-MB and determining the amount of CK-MB in a more directly quantitative manner than achievable by prior art assay methods. The process and immunocomplexes are useful in the diagnosis of myocardial infarction.

DETAILED DESCRIPTION OF THE INVENTION

The present invention relates to a process for immunochemically determining the amount of CK-MB in biological fluid. For the invention processes, it is possible to use biological fluids, e.g. whole blood, plasma, sera, lymph, bile, urine, spinal fluid, sputum, sweat and the like as well as stool excretions of humans or other animals. It is possible also to use fluid preparations of human or other animal tissue such as skeletal muscle, heart, kidney, lungs, brain, bone marrow, skin, and the like. The preferred biological fluid for the invention processes, however, is human serum. The serum in most cases need not be diluted for the invention processes but may be diluted for better results if the amount of CK is unusually high as in the serum of a patient suffering from an acute myocardial infarct. The serum may be diluted with high protein solutions such as heated animal sera as for example heated normal goat or human sera or bovine serum albumin solutions.

Particularly the invention relates to a process for selectively determining directly the amount of CK-MB in a biological fluid sample containing CK-MB in combination with CK-MM and CK-BB. The process comprises (a) incubating the sample with a first antibody raised in a first animal species, the first antibody capable of immunoreactively binding selectively one of the B or M subunits of the creatine kinase in the sample; with a second antibody raised in a second animal species, the second antibody capable of immunoreactively binding selectively as an immunoprecipitin the first antibody; and with a third antibody raised in an animal species other than the first animal species and labeled with a measurable label, the third antibody capable of immunoreactively binding selectively the other of said B or M subunits which the first antibody is capable of binding to provide as a precipitate a mixture of immunocomplexes containing labeled third antibody-creatine kinase-MB isoenzyme-first antibody-second antibody and creatine kinase isoenzyme-first antibody-second antibody; (b) isolating the precipitate; and (c) measuring the amount of label in the immunocomplexes. When the amount of label measured in the immunocomplexes is compared to a standard curve, the amount of CK-MB present in the biological sample is determined.

The invention also relates to a composition for measuring the amount of CK-MB in biological fluid. The composition comprises a first antibody raised in a first animal species and capable of immunoreactively binding selectively one of the B or M subunits of creatine kinase in the sample, a second antibody raised in a second animal species and capable of immunoreactively binding selectively the first antibody, and a third antibody raised in an animal species other than the first animal species, labeled with a measurable label and capable of immunoreactively binding selectively the other of said B or M subunits.

The invention also relates to a diagnostic test kit system for determining the amount of CK-MB in a biological fluid sample. The kit comprises as reagents which may be in packaged combination: (a) a container of a first antibody raised in a first animal species and capable of immunoreactively binding selectively one of the B or M subunits of creatine kinase in the sample, (b) a container of second antibody raised in a second animal species and capable of immunoreactively binding selectively the first antibody, and (c) a container of a third antibody raised in an animal species other than the first animal species, labeled with a measurable label and capable of immunoreactively binding selectively the other of said B or M subunits which the first antibody is capable of binding. Each of the aforementioned antibodies in the kit may be in separate containers. A preferred combination of the antibodies in the kit is that the first antibody and the third antibody are together in a single container while the second antibody is in a separate container.

When all the antibodies of the kit are incubated with the sample precipitable immunocomplexes are provided, the measurement of which determines the amount of CK-MB in the sample by comparison with a standard curve. The test kit would provide all the above antibodies as reagents and may provide also suitable standards thereto for establishing a standard curve. For example, as recognized in the arts, a suitable standard for the test kit may include reagents containing a series of known but different amounts of CK-MB. By measuring the series in a radiometric assay and plotting the measured radioactivity of the series against the known amount of CK-MB, a curve is obtained and can be used as a reference for determining the amount of CK-MB in an unknown sample. The test kit would be suitable for clinics, hospitals, laboratories, and individual physicians having a need to determine CK-MB in fluids.

More particularly, the invention relates to processes by which a test sample such as a serum sample suspected of containing CK-MB is treated with a first antibody immunoreactive with the CK-MB. In one preferred aspect of the invention, the first antibody is produced by immunizing rabbits, a first animal species, with a highly purified CK-BB and obtaining rabbit anti-(CK-BB), the first antibody, by conventional immunological techniques. This particularly first antibody obtained in this manner is capable of binding any B subunit of CK-MB and CK-BB. The first antibody is mixed and incubated with the test sample for approximately 5 minutes at room temperature and, thereby, binds immunologically any CK-MB and CK-BB of the sample to provide a CK-MB first antibody and CK-BB—first antibody complexes. The amount of first antibody used is an amount sufficient to bind all the CK-MB of the test sample, not withstanding that the first antibody will also bind any CK-BB present in the sample. First antibody added in an amount in excess of that required to bind all the CK-MB and CK-BB in the sample is essential for the best determination of CK-MB in the test sample. The determination of the amount of the first antibody needed can be determined by well recognized procedures in this art.

The test sample is then treated with a second antibody immunoreactive as an immunoprecipitin with the first antibody. The second antibody is produced by immunizing goats, a second animal species, with rabbit gammaglobulin (IgG) and obtaining goat anti-rabbit IgG, the second antibody, by conventional immunological techniques. The second antibody, obtained in this manner is capable of binding any rabbit IgG, including therefore rabbit anti-(CK-BB). The second antibody is mixed and incubated with the test sample for approximately 5 minutes at room temperature, and thereby binds immunologically the first antibody. This provides as a precipitate an immunoprecipitin containing CK-MB-first antibody-second antibody and CK-BB-first antibody-second antibody. The amount of second antibody used is an amount sufficient to bind all the first antibody. Second antibody added in an amount in excess of that required to bind all the first antibody is essential for the best determination of CK-MB in the test sample.

A solution of normal saline is then added to the test sample, the sample centrifuged, and the supernatant removed by decanting. This decanting procedure separates from the immunoprecipitin any CK-MM which would otherwise interfere in the procedure.

The immunoprecipitin is then treated with a solution of a third antibody immunoreactive at this point in the process exclusively with any CK-MB of the immunoprecipitin. The third antibody may bind isoenzymes other than CK-MB in the test fluid, but as to the immunoprecipitin the third antibody is immunoreactive only with CK-MB, even though the immunoprecipitin may contain isoenzymes other than CK-MB. The invention has the advantage that it can be carried out using a sample containing isoenzymes other than CK-MB immunoreactive with the antibodies comprising the invention.

The third antibody is produced by immunizing sheep, an animal species other than the first animal species, with highly purified CK-MM and obtaining sheep anti-(CK-MM), the third antibody, by conventional immunological techniques. The third antibody is purified and then iodinated with Iodine-125 to provide a third antibody labeled with a measurable label. The third antibody obtained in this manner is capable of binding any M subunit of CK-MB and CK-MM. The third antibody in solution is added to the immunoprecipitin in a known concentration. The third antibody is mixed and incubated with the immunoprecipitin for approximately 30 minutes at room temperature, providing thereby as a precipitate a mixture of immunocomplexes, containing labeled third antibody-CK-MB-first antibody-second antibody and CK-BB-first antibody-second antibody. The resulting mixture is diluted with saline, centrifuged and decanted. The centrifugation and decanting isolates the precipitate containing the immunocomplexes from other interfering substances. The immunocomplexes may be collected and isolated by any art recognized procedure such as filtration. The preferred procedure is centrifugation and decanting. The radioactivity associated with the immunocomplexes in the precipitate is then determined in a gamma scintillation counter. The radioactivity observed will be essentially proportional to the amount of CK-MB in the test sample.

An alternative process to the foregoing procedure is to mix each antibody successively with the test sample, separate the resulting radioactive precipitate containing the immunocomplexes and then determine the radioactivity associated with the complexes.

In another preferred aspect of the invention, the first antibody is produced by immunizing rabbits with highly purified CK-MM and obtaining rabbit anti-(CK-MM), the first antibody, by conventional immunological techniques. The first antibody obtained in this manner is capable of binding any M subunit of CK-MB or CK-MM. The third antibody is produced by immunizing sheep with highly purified CK-BB and obtaining sheep anti-(CK-BB) which is purified and labeled with iodine-125, providing thereby a third antibody with a measurable label. The third antibody obtained in this manner is capable of binding any B subunit of CK-MB or CK-BB. The second antibody is the same as described earlier. The first antibody and the third antibody are added to the test sample which is thereafter mixed and incubated for approximately 1 hour at room temperature. The second antibody is then added to the test sample which is then mixed and incubated again for 15 minutes at room temperature. Subsequently the test sample is diluted with saline, centrifuged, and the supernatant decanted. The radioactivity of the precipitate containing the resulting radioactive immunocomplexes is determined as described earlier.

The isoenzymes namely CK-MM and CK-BB, employed as antigens to raise the first and third antibodies, can be obtained from any suitable biological fluid such as blood serum or biological organ or tissue such as cardiac muscle, skeletal muscle, bone marrow, or any other organ tissue known to have these isoenzymes. The preferred source of these isoenzymes is animal skeletal muscle and brain.

Purification of the aforementioned isoenzymes to a state of high purity before using them for raising antibodies is most advisable in order to diminish the presence of non-specific antibodies. The isoenzymes may be purified by any conventional purification procedure recognized in the art for such purposes. The preferred purification procedure encompasses conventional art recognized procedures such as alcohol fractionation and anion exchange chromatography.

The degree of high purity of the isoenzymes used to raise the antibodies as well as the specificity of the resulting antibodies can be determined by currently acceptable practices in the art such as by immunodiffusion or electrophoretic techniques. The preferred method for purity of the isoenzymes is acrylamide gel electrophoresis.

The purified CK-MM and CK-BB can be employed as antigens to raise the first antibody and third antibody in various animals, especially in vertebrates e.g. pigs, cattle, horses, sheep, goat, dogs, monkeys, rabbits, birds, guinea pigs, rats, etc. Among these animals, mammals such as the rabbit, sheep, and goat, are preferred.

The second antibody or precipitating antiserum can be obtained by employing the first antibody as an antigen in the various aforementioned animal species. It is essential however that the first and second antibodies be raised in different animal species, inorder that the second antibody be specific in the test sample for the first antibody. The second antibody is directed against the gammaglobulin (IgG) of the animal species in which the first antibody was raised.

As an alternate approach to the embodiment of this invention, the second antibody may be insolubilized by attaching the second antibody to an insoluble support material. Suitable support materials include water insoluble organic polymeric substances such as cellulose or other polysaccharide, a vinyl addition polymer or condensation polymer or a water soluble inorganic substance of polymeric nature, such as glass or silicone resins. On the other hand the second antibody may be adsorbed to the surface of a solid support such as polystyrene, polypropylene, polyfluorethylene or polyvinylidene fluoride. The method of attachment of the second antibody to the solid support is not critical and may include (1) covalently coupling the soluble second antibody to an insoluble polymerized form, such as by reaction with an insolubilizing agent; (3) physical entrapment of particles of the second antibody in the pores of a gel polymer such as a cross-linked polyacrylamide; or (4) by physical adsorption on an insoluble polymeric substance. Where a solid support is used the preferred embodiment is that the second antibody be attached by adsorption on activated polyvinylidene fluoride (Kynar) utilizing the general procedures well known in the art such as the procedure disclosed in U.S. Pat. No. 3,843,443.

The third antibody may be raised in any aforementioned animal other than the species from which the first antibody is obtained. The preferred source of the first antibody is rabbit, the second antibody is goat, and the third antibody is sheep. The raising of antibodies to the isoenzymes CK-MM and CK-BB is by any conventional methods known in this art.

The third antibody may be labeled for assay purposes by any art recognized procedures employing any art recognized label such as enzymatic, chemiluminescent, fluorescent or radioisotopic. The preferred label is radioisotopic for a radiometric assay procedure. Any suitable art recognized radioisotope may be employed as a label. The preferred radioisotope is iodine-125, which can be used to label the third antibody of this invention by any of the art recognized procedures.

The radioactivity that is associated with the radioactive immunocomplexes of this invention as determined by a radiometric assay is proportional to the amount of CK-MB in the test sample when compared with an appropriate standard curve. As recognized in the art for example an appropriate standard curve may be obtained by radiometric assay of samples obtained by serial dilution of a known concentration of CK-MB. The measured radioactivity in each sample is plotted against the concentration of CK-MB in each sample to provide a curve. This curve serves as a reference for determining the concentration of CK-MB in an unknown sample.

The following Examples further illustrate the invention but are not meant to limit the invention in scope or spirit.

EXAMPLE I

CK Isoenzyme Purification

CK isoenzymes were purified according to the method of Elaine Carlson, Robert Roberts, and Burton E. Sobel. J. Molecular and Cellular Cardiology 8: 159–167 (1976).

EXAMPLE II

Antibody production

Rabbits were immunized weekly with 0.5 mg of purified CK-MM or 1 mg CK-BB. The immunogen was emulsified in complete Freund's adjuvant and injected subcutaneously in the axillary area at two sites. The rabbits were bled monthly.

Goats or sheep were immunized with 2 mg of purified CK-MM or CK-BB on a weekly basis. The immunogen was emulsified in complete Freund's adjuvant and administered subcutaneously in the axillary regions. The goats or sheep were bled every two weeks.

EXAMPLE III

Antibody Purification

In order to purify the antibody by affinity Chromatography, the CK-MM or CK-BB were coupled to CNBr-Activated Sepharose 4B gel.

Materials for Coupling to Sepharose 4B were the following:
1. CNBr-Activated Sepharose 4B (Pharmacia).
2. Purified CK-BB or CK-MM, approximately 5 mg.
3. $10^{-3}$ M HCl.
4. 0.1 M NaHCO$_3$ buffer containing 0.5 N NaCl
5. 1 M Ethanolamine in 0.1 M NaHCO$_3$ buffer with 0.5 M NaCl, pH 8.0.
6. 0.1 M Acetate buffer containing 1 M NaCl, pH 8.0.
7. 0.1 M Borate buffer containing 1 M NaCl, pH 8.0.
8. 0.1 M PBS, pH 7.2 with 0.1% NaN$_3$.
9. Fisher Rotorack
10. Sorval RC-3 refrigerated centrifuge
11. Spectrophotometer
12. Amicon ultrafiltration cells.
13. Lowry protein determination reagents.

Procedure for coupling to Sepharose 4B gel was as follows:
1. 0.5 g CNBr-activated Sepharose 4B gel was placed in 200 ml $10^{-3}$ M HCl for 15 minutes. The gel was transferred to a scintered glass funnel and washed for about 15 minutes more with an additional 200 ml HCl.
2. The purified isoenzyme (approximately 5 mg in 5 ml) was dialyzed against the NaHCO$_3$ buffer at 4° C. for 3 hours with several changes of the buffer.
3. The swollen gel and the isoenzyme solution were placed in a test tube, capped and rotated slowly end-over-end overnight at 4° C. on the rotorack.
4. Unbound material was washed away with three 20 ml washes of NaHCO$_3$ buffer. Each wash cycle was centrifuged at 1200×g for 5 minutes. The OD 280 nm of the supernatant fluid was determined. Washes which had OD 280 nm greater than 0.5 were combined and retained for analysis.
5. Ten ml of 1 M Ethanolamine solution was placed in the test tube with the gel and rotated end-over-end for 3.5 hours at 4° C. to react any remaining active groups.
6. Three wash cycles were used to remove non-covalently adsorbed protein. Each wash consisted of 20 ml acetate buffer, pH 4.0. Each wash was centrifuged at 1200×g for 5 minutes and the supernatant discarded. This was followed by one 20 ml wash with Borate buffer, pH 8.0.
7. The gel was washed twice with 20 ml PBS and the resulting supernatants discarded. The coupled isoenzyme-Sepharose 4B was stored in PBS at 4° C.
8. Supernatants from step 2 were concentrated to original volume and protein concentration determined by Lowry in order to establish coupling efficiency.

Materials for purification of the antiserum by affinity chromatography were as follows:
1. CK-BB or CK-MM Sepharose 4B gel
2. Anti-CK-BB or CK-MM serum
3. Fisher Rotorack
4. Sorvall Rc-3 refrigerated Centrifuge.
5. 3.0 M Ammonium thiocyanate.
6. Deionized water
7. 0.05 M sodium phosphate buffer, pH 7.5

Procedure for purification of the antiserum by affinity chromatography was as follows:
1. 2–5 ml of antiserum was added to 0.5 g CK-BB or CK-MM-sepharose 4B in a test tube. The mixture was rotated end-over-end on the rotorack for 1 hour at room temperature.
2. The tube was centrifuged at 1200×g for 5 minutes. The supernatant was removed but retained as the "unreacted" protein for analysis. The sepharose 4B pellet residue remaining in the tube was washed with PBS until the OD 280 nm of the decanted supernatant was less than 0.05.
3. To the tube containing the sepharose was added ammonium thiocyanate to a final concentration of 2.5 M. The resulting mixture was rotated end-over-end for 15 minutes at room temperature. The tube was centrifuged at 1200×g for 5 minutes. The supernatant was immediately withdrawn and dialyzed against deionized water at 4° C. for 1.5 hours. The affinity purified antibody was then extensively dialyzed (approximately 48 hours) against phosphate buffer at 4° C. to remove any remaining thiocyanate.
4. After dialysis, the affinity purified antibody was concentrated by ultrafiltration to original volume. Protein concentration was determined by the Lowry method and antibody activity was determined by the ability to bind a fixed amount of purified CK-MM or CK-BB.

EXAMPLE IV

Materials for iodination of affinity purified antibody were as follows:
1. Anti-(CK-BB) or anti-(CK-MM) with protein concentration approximately 1 mg per ml.
2. Na$^{125}$I (Amersham).
3. Chloramine-T, 5 mg per ml in 0.05 M sodium phosphate, pH 7.5.
4. Sodium metabisulfite, 10 mg per ml in 0.05 M sodium phosphate, pH 7.5
5. 5% Bovine serum albumin (BSA) solution (w/v in deionized H$_2$O).
6. 0.3 ml Reacti-Vial.
7. 1×30 cm column of Sephadex G-100 equilibrated in 0.1 M Tris-HCl, pH 7.5 with 0.15 M NaCl and 0.02% NaN$_3$.

Procedure for iodination of purified antibody was as follows:

1. The following were added in sequence to the Reacti-Vial: 50 μg Antibody, 5 μl $^{125}$I, and 5 μl chloramine-T. The vial was vortexed for 60 seconds followed by the addition of 5 μl sodium metabisulfite. The vial was vortexed an additional 30 seconds.
2. 125 μl of a 5% BSA were added and the vial vortexed again.
3. The reaction mixture was applied to the sephadex column. The column was eluted with Tris buffer at a flow rate of approximately 20 ml per hour. A total of 30 1.5 ml fractions were collected. 20 μl aliquots of each fraction were counted in a gamma scintillation counter. Fractions constituting the first peak of the chromatograph were pooled and stored at 4° C.

EXAMPLE V

Preparation of CK-MB standards was as follows:

1. CK-MB was purified from human heart tissue according to the procedure of Carlson et al. Purified CK-MB was stored in 0.05 M Tris-HCl buffer, pH 7.5, at 4° C. in concentrations exceeding 30 mg/ml.
2. CK-MB standards were prepared at the following concentrations by diluting in normal goat serum: 14 ng/ml, 28 ng/ml, 70 ng/ml, 140 ng/ml, 280 ng/ml and 700 ng/ml. The CK-MB standards can be lyophilized for long term storage.

EXAMPLE VI

Radiometric Assay Procedure

A. Procedure for using labeled Sheep anti-(CK-MM) is as follows:

1. Add 200 μl sample (CK-MB standard or clinical serum sample) to a test tube.
2. Add 50 μl of Rabbit anti-(CK-BB) serum.
3. Vortex tubes and incubate 5 minutes at room temperature.
4. Add 200 μl of goat anti-rabbit IgG. Mix tubes and incubate 5 minutes at room temperature.
5. Add 5 ml normal saline solution to test tube.
6. Centrifuge tubes and decant supernatant.
7. Add 200 μl $^{125}$I-Sheep anti-(CK-MM) (approximately 100,000 CPM) to the Pellet. Incubate 30 minutes at room temperature with shaking.
8. Add 5 ml normal saline solution to test tubes.
9. Centrifuge to obtain pellet.
10. Decant supernatant
11. Count pellet in gamma scintillation counter.

Table I represents values for a standard curve from a CK radiometric assay detecting CK-MB. The data was obtained from reactions run according to the disclosures of Examples V and VI (A) and illustrate the usefulness of the invention process for determining CK-MB in a test sample.

TABLE I

| CK-MB ng/ml | CPM Data |
|---|---|
| 0 | 4740 |
| 28 | 5281 |
| 70 | 6239 |
| 140 | 8305 |
| 280 | 11592 |
| 700 | 21412 |

B. Procedure for using labeled sheep anti-(CK-BB) is as follows:

1. Add 500 μl sample (CK-MB standard or clinical serum sample) to a test tube.
2. Add 100 μl of antibody mix, consisting of rabbit anti-(CK-MM) and $^{125}$I-sheep anti-(CK-BB) antisera (200,000 CPM) and vortex tubes.
3. Incubate 1 hour at room temperature.
4. Add 200 μl goat anti-rabbit IgG.
5. Vortex tubes and incubate 15 minutes at room temperature.
6. Add 4.0 ml normal saline solution.
7. Centrifuge to obtain pellet.
8. Decant supernatant
9. Count pellet in gamma scintillation counter.

Table II represents values for a standard curve from a CK radiometric assay detecting CK-MB. The data was obtained from reactions run according to the disclosures of Example V and VI (B) and illustrate the usefulness of the invention process for determining CK-MB in a test sample.

TABLE II

| CK-MB ng/ml | CPM Data |
|---|---|
| 0 | 6912 |
| 28 | 11840 |
| 70 | 18580 |
| 140 | 26375 |
| 280 | 38840 |
| 700 | 58456 |

We claim:

1. A process for determining the amount of creatine kinase-MB isoenzyme in a biological fluid sample containing creatine kinase having subunit B or M or both, the process comprising:
   (a) incubating the sample with
      (i) a first antibody raised in a first animal species, the first antibody capable of immuno-reactively binding selectively one of the B or M subunits of the creatine kinase in the sample;
      (ii) a second antibody raised in a second animal species, the second antibody capable of immunoreactively binding selectively as an immunoprecipitin with the first antibody; and
      (iii) a third antibody raised in an animal species other than the first animal species and labeled with a measurable label, the third antibody capable of immunoreactively binding selectively with the other of said M or B subunits
   to provide as a precipitate a mixture of immuno-complexes containing labeled third antibody-creatine kinase-MB isoenzyme-first antibody-second antibody and creatine kinase isoenzyme-first antibody-second antibody;
   (b) isolating the precipitate containing the immunocomplexes;
   (c) measuring the amount of label in the precipitate; and
   (d) comparing the amount of measured label to a standard curve thereby determining the amount of creatine kinase-MB isoenzyme in the biological fluid sample.

2. A process according to claim 1 wherein the third antibody has a radioactive label.

3. A process according to claim 2 wherein the radioactive label is iodine-125.

4. A process according to claim 1 wherein the biological fluid sample is blood serum.

5. A process according to claim 4 wherein the blood serum is derived from a patient suspected of a myocardial infarct.

6. A process according to claim 1 wherein the first, second, and third antibodies are each obtained from different animal species.

7. A process according to claim 6 wherein the first antibody is rabbit anti-(CK-MM), the second antibody is goat anti-rabbit IgG, and the third antibody is sheep anti-(CK-BB).

8. A process according to claim 6 wherein the first antibody is rabbit anti-(CK-BB), the second antibody is goat anti-rabbit IgG, and the third antibody is sheep anti-(CK-MM).

9. A process according to claim 1 wherein the second antibody is attached to an insoluble solid support material.

10. A process for determining the amount of creatine kinase-MB isoenzyme in a biological fluid sample containing creatine kinase having subunits B or M or both, the process comprising:
   (a) incubating the sample with
      (i) a first antibody raised in a first animal species, the first antibody capable of immunoreactively binding selectively the B subunit of the creatine kinase in the sample, and
      (ii) a second antibody raised in a second animal species, the second antibody capable of immunoreactively binding selectively as an immunoprecipitin with the first antibody
   to provide as an immunoprecipitin a mixture containing creatine kinase-MB isoenzyme-first antibody-second antibody and creatine kinase-BB isoenzyme-first antibody-second antibody;
   (b) isolating the immunoprecipitins from the mixture,
   (c) incubating the isolated immunoprecipitins with a third antibody raised in an animal species other than the first animal species and labeled with a measurable label, the third antibody capable of immunoreactively binding selectively with the M subunit of the creatine-kinase-MB isoenzyme to provide as a precipitate a mixture of immunocomplexes containing labeled third antibody creatine kinase-MB isoenzyme-first antibody-second antibody and creatine kinase-BB isoenzyme-first antibody-second antibody;
   (d) isolating the precipitate containing the immunocomplexes;
   (e) measuring the amount of label in the precipitate; and
   (f) comparing the amount of measured label to a standard curve thereby determining the amount of creatine kinase-MB isoenzyme in the biological fluid sample.

11. A process according to claim 10 wherein the third antibody has a radioactive label.

12. A process according to claim 11 wherein the radioactive label is iodine-125.

13. A process according to claim 10 wherein the biological fluid sample is blood serum.

14. A process according to claim 13 wherein the blood serum is derived from a patient suspected of a myocardial infarct.

15. A process according to claim 10 wherein the first, second, and third antibodies are each obtained from different animal species.

16. A process according to claim 15 wherein the first antibody is rabbit anti-(CK-BB), the second antibody is goat anti-rabbit IgG, and the third antibody is sheep anti-(CK-MM).

17. A process according to claim 10 wherein the second antibody is attached to an insoluble solid support material.

18. A process for determining the amount of creatine kinase-MB isoenzyme in a biological fluid sample containing creatine kinase having subunits B or M or both, the process comprising:
   (a) incubating the sample with
      (i) a first antibody raised in a first animal species, the first antibody capable of immunoreactively binding selectively with the M subunit of the creatine kinase in the sample, and
      (ii) a third antibody raised in an animal species other than the first animal species and labeled with a measurable label, the third antibody capable of immunoreactively binding selectively with the B subunit of the creatine kinase in the sample to provide a mixture of immunocomplexes containing labeled third antibody-creatine kinase-MB isoenzyme first antibody; labeled third antibody-creatine kinase-BB isoenzyme; and creatine kinase-MM isoenzymefirst antibody;
   (b) incubating the mixture with a second antibody raised in a second animal species, the second antibody capable of immunoreactively binding selectively as an immunoprecipitin with the first antibody to provide as a precipitate a mixture of immunocomplexes containing labeled third antibody-creatine kinase-MB isoenzymefirst antibody-second antibody and creatine kinase-MM isoenzyme-first antibody-second antibody;
   (c) isolating the precipitate containing immunocomplexes;
   (d) measuring the amount of label in the precipitate; and
   (e) comparing the amount of measured label to a standard curve thereby determining the amount of creatine kinase-MB isoenzyme in the biological fluid sample.

19. A process according to claim 18 wherein the third antibody has a radioactive label.

20. A process according to claim 19 wherein the radioactive label is iodine-125.

21. A process according to claim 18 wherein the biological fluid sample is blood serum.

22. A process according to claim 21 wherein the blood serum is derived from a patient suspected of a myocardial infarct.

23. A process according to claim 18 wherein the first, second, and third antibodies are each obtained from different animal species.

24. A process according to claim 23 wherein the first antibody is rabbit anti-(CK-MM), the second antibody is goat antirabbit IgG, and the third antibody is sheep anti-(CK-BB).

25. A process according to claim 18 wherein the second antibody is attached to an insoluble solid support material.

26. A composition for measuring the amount of creatine kinase-MB isoenzyme in biological fluid sample containing creatine kinase having subunits B or M or both, the composition comprising a first antibody raised in a first animal species and capable of immunoreactively binding selectively one of the B or M subunits of creatine kinase in the sample; a second antibody raised in a second animal species and capable of immunoreactively binding selectively as an immunoprecipitin the first antibody, and a third antibody raised in an animal species other than the first animal species, labeled with a measurable label and capable of immunoreactively binding selectively the other of said M or B subunits.

27. A composition according to claim 26 wherein the third antibody has a radioactive label.

28. A composition according to claim 27 wherein the radioactive label is iodine-125.

29. A composition according to claim 26 wherein the biological fluid sample is blood serum.

30. A composition according to claim 26 wherein the first, second and third antibodies are obtained from different animal species.

31. A composition according to claim 30 wherein the first antibody is rabbit anti-(CK-BB), the second antibody is goat anti-rabbit IgG, and the third antibody is sheep anti-(CK-MM).

32. A composition according to claim 30 wherein the first antibody is rabbit anti-(CK-MM), the second antibody is goat anti-rabbit IgG, and the third antibody is sheep anti-(CK-BB).

33. A composition according to claim 26 wherein the second antibody is attached to an insoluble support material.

34. A diagnostic test kit system for determining the amount of creatine kinase-MB isoenzyme in an immunoassay, the test kit system comprising in combination:
  (a) a container of a first antibody raised in a first animal species and capable of immunoreactively binding selectively one of the B or M subunits of creatine kinase,
  (b) a container of a second antibody raised in a second animal species and capable of immunoreactively binding selectively as an immunoprecipitin the first antibody, and
  (c) a container of a third antibody raised in an animal species other than the first animal species, labeled with a measurable label and capable of immunoreactively binding selectively the other of said M or B subunits bound by the first antibody,
all of said antibodies being immunoreactive binders and present in relative amounts sufficient to provide an immunocomplex containing creatine kinase-MB isoenzyme selectively bound to all three of said antibodies.

35. A test kit system according to claim 34 wherein the third antibody has a radioactive label.

36. A test kit system according to claim 35 wherein the radioactive label is iodine-125.

37. A test kit system according to claim 34 wherein the biological fluid sample is blood serum.

38. A test kit system according to claim 34 wherein the first, second, and third antibodies are each obtained from different animal species.

39. A test kit system according to claim 38 wherein the first antibody is rabbit anti-(CK-MM), the second antibody is goat anti-rabbit IgG, and the third antibody is sheep anti-(CK-BB).

40. A test kit system according to claim 38 wherein the first antibody is rabbit anti-(CK-BB), the second antibody is goat anti-rabbit IgG, and the third antibody is sheep anti-(CK-MM).

41. A test kit system according to claim 34 wherein the second antibody is attached to an insoluble solid support material.

42. A test kit system according to claim 34 wherein the first antibody and the third antibody are in the same container.

43. A test kit system according to claim 34 further comprising standards for establishing a standard curve.

* * * * *